United States Patent
Powell et al.

(10) Patent No.: US 11,267,836 B2
(45) Date of Patent: *Mar. 8, 2022

(54) METHODS FOR PRODUCING FERRIC MALTOL COMPOSITIONS FROM LIGAND MODIFIED AND LIGAND COATED FERRIC HYDROXIDES

(71) Applicant: Shield TX (UK) Limited, Gateshead (GB)

(72) Inventors: Jonathan Joseph Powell, Cambridge (GB); Nuno Jorge Rodrigues Faria, Milton Ernest (GB)

(73) Assignee: SHIELD TX (UK) LIMITED, Tyne and Wear (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/089,764

(22) PCT Filed: Mar. 31, 2017

(86) PCT No.: PCT/EP2017/057691
§ 371 (c)(1),
(2) Date: Sep. 28, 2018

(87) PCT Pub. No.: WO2017/167963
PCT Pub. Date: Oct. 5, 2017

(65) Prior Publication Data
US 2019/0106449 A1    Apr. 11, 2019

(30) Foreign Application Priority Data
Mar. 31, 2016 (GB) ...................... 1605470

(51) Int. Cl.
*C07D 309/40* (2006.01)
*C07F 15/02* (2006.01)

(52) U.S. Cl.
CPC .......... *C07F 15/025* (2013.01); *C07D 309/40* (2013.01)

(58) Field of Classification Search
CPC ................................. C07F 15/025
USPC ........................................ 549/210
See application file for complete search history.

(56) References Cited

U.S. PATENT DOCUMENTS

| | | | | |
|---|---|---|---|---|
| 5,177,068 A * | 1/1993 | Callingham | ......... | C07D 213/69 514/184 |
| 7,459,569 B2 * | 12/2008 | Stockham | ............ | C07D 309/40 549/210 |
| 8,058,462 B2 * | 11/2011 | Powell | .................. | C07F 15/025 556/138 |
| 2008/0188555 A1 | 8/2008 | Powell et al. | | |
| 2017/0130077 A1 * | 5/2017 | Zong | ......................... | C09D 7/48 |
| 2018/0370903 A1 * | 12/2018 | Sercheli | ............... | A61K 31/295 |

FOREIGN PATENT DOCUMENTS

| | | | | |
|---|---|---|---|---|
| CN | 103382151 B | * | 7/2013 | ............. C07C 51/41 |
| WO | WO 03/097627 | | 11/2003 | |
| WO | WO 2008/096130 | | 8/2008 | |
| WO | WO 2012/101442 | | 8/2012 | |
| WO | WO 2015/101971 | | 7/2015 | |

OTHER PUBLICATIONS

Muir, European journal of soil science, 1964, 15(2), 226-237.*
Elgala, Journal of Plant Nutrition, 11 (6-11), 677-690 (1988), p. 678.*
Gerard, STN Abstractor Journal of Chemical Research, Synopses (1980), (9), 314.*
International Search Report and Written Opinion issued in International Application No. PCT/EP2017/057691, dated May 12, 2017.
Search Report issued in United Kingdom Application No. GB 1605470.2, dated Jan. 20, 2017.
Gasche, Christoph, et al. "Ferric maltol is effective in correcting iron deficiency anemia in patients with inflammatory bowel disease: results from a phase-3 clinical trial program." *Inflammatory bowel diseases* 21.3 (2014): 579-588.
Harvey, R. S. J., et al. "Ferric trimaltol corrects iron deficiency anaemia in patients intolerant of iron." *Alimentary pharmacology & therapeutics* 12.9 (1998): 845-848.

* cited by examiner

*Primary Examiner* — Nizal S Chandrakumar
(74) *Attorney, Agent, or Firm* — Parker Highlander PLLC

(57) ABSTRACT

Methods for producing ferric maltol compositions, such as ferric trimaltol, are described in which maltol is reacted with a ligand modified ferric hydroxide and/or a ligand coated ferric hydroxide.

12 Claims, 2 Drawing Sheets

METHODS FOR PRODUCING FERRIC MALTOL COMPOSITIONS FROM LIGAND MODIFIED AND LIGAND COATED FERRIC HYDROXIDES

This application is a national phase application under 35 U.S.C. § 371 of International Application No. PCT/EP2017/057691, filed Mar. 31, 2017, which claims priority to United Kingdom Application No 1605470.2 filed Mar. 31, 2016. The entire text of each of the above referenced disclosures is specifically incorporated herein by reference.

FIELD OF THE INVENTION

The present invention relates to methods for producing ferric maltol compositions, such as ferric trimaltol, from ligand modified or ligand coated ferric hydroxides, and to ferric maltol compositions produced by these methods and their uses.

BACKGROUND OF THE INVENTION

The sugar derivative maltol is a hydroxypyrone (IUPAC name: 3-hydroxy-2-methyl-4H-pyran-4-one) and it strongly chelates iron and the resulting complex (ferric trimaltol) is well absorbed, unlike many other ferric iron therapies. Ferric trimaltol appears well tolerated even in populations highly susceptible to gastrointestinal side-effects, such as IBD patients (Harvey et al., 1998), and as such it provides a valuable alternative to patients who are intolerant of oral ferrous iron products, notably in place of intravenous iron. Clinical trials using ferric trimaltol have been carried out, see for example, Gasche et al., 2015.

However, despite the evidence of bioavailability and tolerability for ferric trimaltol, its clinical development has been limited by the absence of adequate synthetic routes. In particular, most manufacturing processes require the use of organic solvents, which increase manufacturing costs, for example to deal with post-synthesis solvent removal, and require additional safety measures, for example to deal with flammability. Critically, solvent-based syntheses are not robust and often generate ferric hydroxide, described in the prior art to be an unwanted impurity of the synthesis.

WO 03/097627 (Vitra Pharmaceuticals Limited) describes the synthesis of ferric trimaltol from iron salts of carboxylic acids in aqueous solution at a pH greater than 7. In a first synthesis, ferric citrate is added to a solution of sodium hydroxide at room temperature and maltol is added to a second solution of sodium hydroxide at pH 11.6. The ferric citrate solution is added to the maltol solution, leading to the production of a deep red precipitate. This composition is then evaporated until dryness and the material is powdered and dried. Alternative syntheses are described using ferrous fumarate or ferrous gluconate as the iron carboxylate salt starting material, and by dissolving maltol in sodium carbonate solution in place of sodium hydroxide. However, despite the fact that this process is fully aqueous, several of the iron carboxylate salts employed are expensive, especially as they need to be pharmaceutical grade if the ferric trimaltol is to be suitable for human administration. More importantly, this process introduces high levels of carboxylates (equimolar to iron or greater) to the synthesis that are not easily removed by filtration or centrifugation of the ferric trimaltol cake. Instead these water soluble contaminants must be washed off (e.g. water washed), but this would result in considerable losses of the product due to the amphipathic nature of ferric trimaltol.

WO 2012/101442 (Iron Therapeutic Holdings AG) describes the synthesis of ferric trimaltol by reacting maltol and a non-carboxylate iron salt in an aqueous solution at alkaline pH. However, despite the lower cost of non-carboxylate iron salts, pharmaceutically appropriate grades are still required if the ferric trimaltol is to be suitable for human administration and hence are comparatively expensive starting materials.

Importantly, the use of non-carboxylate iron salts (e.g. ferric chloride) results in the addition of considerable levels of the respective counter-anion (e.g. three moles of chloride per every mole of iron) of which a significant part is retained in the filtration (or centrifugation) cake and thus must be washed off. As such, WO 2012/101442 does not address the problem of product losses in WO 03/097627. Furthermore, the addition of a non-carboxylate iron salt (e.g. ferric chloride) to a very alkaline solution, as described in WO 2012/101442, promotes the formation of stable iron oxides, which is an unwanted contaminant in ferric trimaltol. As a consequence, further costly and time-consuming processing of the material would be required for manufacturing.

Overall, the cost of the current aqueous syntheses is driven by regulatory demands for low levels of toxic heavy metals and residual reagents in the final pharmaceutical formulation, which force the use of highly purified, and thus expensive, iron salts as well as thorough washing of the final product (resulting in significant losses of product). This will impact on the final price of ferric trimaltol and potentially limits patient access to this therapy. As such, there is a need for a process that can use lower iron grades and limited wash cycles, whilst producing ferric trimaltol of adequate purity.

Accordingly, it remains a problem in the art to provide processes for the synthesis of ferric trimaltol at economic cost and which overcome some or all of the drawbacks set out above that are associated with prior art synthetic methods. Solving these issues, through better synthesis of the material would allow good patient access to ferric trimaltol.

SUMMARY OF THE INVENTION

Broadly, the present invention relates to methods for producing ferric maltol compositions, such as ferric trimaltol, in which maltol is reacted with a ligand modified ferric hydroxide or, additionally or alternatively, a ligand coated ferric hydroxide. The present invention surprisingly shows that ferric hydroxide, which is commonly claimed to be an unwanted by-product in prior art ferric trimaltol syntheses, and is often present as a contaminant in ferric trimaltol compositions, is in fact capable of being an effective source of iron in the synthesis of ferric maltols, provided that the teachings of the present invention are followed by using ligand modified ferric hydroxide or ligand coated ferric hydroxide, and preferably by using these ferric hydroxide materials when freshly precipitated.

Accordingly, in a first aspect, the present invention provides a method for producing a ferric maltol composition comprising reacting ligand modified or ligand coated ferric hydroxide with maltol and recovering the ferric maltol that forms. In a preferred embodiment, the present invention provides a method for producing a ferric trimaltol composition comprising reacting ligand modified or ligand coated ferric hydroxide with maltol and recovering the ferric trimaltol that forms.

Advantageously, the ligand modified and ligand coated ferric hydroxides are typically recovered at pHs that are too acidic (e.g. pHs below 6, or more preferably pHs below 4.5) for the precipitation of several toxic heavy metals, e.g.

cadmium or arsenic, that may have been present as contaminants in the starting materials. Consequently, the recovered ferric hydroxide compositions when the ferric hydroxide is separated from supernatant may be expected to contain lower levels of toxic elements than an equivalent ferric iron salt used in the syntheses described in the prior art.

Additionally or alternatively, the methods of the present invention that are described herein may provide the further advantage of enabling syntheses from ligand modified or ligand coated ferric hydroxides produced from elemental iron, thereby enabling ferric maltol to be produced from the most inexpensive source of iron, e.g. as compared to the more expensive iron salts used as starting materials in WO 03/097627 and WO 2012/101442. A still further advantage is that the methods for producing ferric maltol according to the present invention may enable single vessel synthesis, for example using a single manufacturing vessel, such as a filtration unit with overhead stirring.

Furthermore, in contrast to prior art processes (e.g. WO 03/097627), the synthesis described herein does not require the introduction of counter-anionic ligands of iron salts (e.g. carboxylates such as citrate), nor inorganic counter anions of iron salts (e.g. chloride as per process described in WO 2012/101442). Therefore, the process is advantageous since it produces materials with lower levels of contaminants and thus subsequent wash cycles need not be extensive.

In the synthetic process described herein, some ligand (e.g. carboxylate) is also added to the synthesis but here the carboxylate concentrations used are sub-stoichiometric and thus considerably lower than in prior art processes (e.g. WO 03/097627). Importantly, only a fraction of the ligand is incorporated with the rest being easily washed off from the ferric hydroxide material prior to addition to the maltol solution or slurry. Therefore, the methods described herein are advantageous since considerably lower levels of ligand are introduced in the synthesis than in previously disclosed processes.

Taken together, the methods of the present invention enable unwanted solutes to be removed from ferric hydroxide in single vessel syntheses from elemental iron (zero valence). This is highly advantageous as it enables the production of high purity ferric maltol compositions in a straightforward manner from a cheaper source of iron (i.e. elemental iron) to that required in the prior art.

In contrast, without the formation of ferric hydroxide intermediates used in the methods of the present invention, single vessel syntheses based on forming soluble non-carboxylate iron salts (e.g. ferric chloride) from elemental iron are not commercially practical, since the large concentration of unwanted salts formed or added during the synthesis (e.g. chloride from hydrochloric acid) contaminate the product and are not easily removed. In addition, a single vessel synthesis in which soluble iron carboxylate salts (e.g. ferric citrate) are formed for subsequent conversion to ferric trimaltol would not be industrially feasible since dissolution of elemental iron by carboxylates is orders of magnitude slower than with strong mineral acids and the clean-up of unwanted solutes would not be practical. In the present invention, unreacted iron may be easily removed with a magnet.

In some aspects, the maltol used in the methods of the present invention is provided as a slurry or a suspension. In this situation, the reaction between the ligand modified or ligand coated ferric hydroxide releases hydroxyl ions as the ferric iron ions are complexed by maltol, leading to the dissolution of further maltol in the slurry. This cycle of the release of hydroxyl ions causing maltol to dissolve has the advantage that the pH of the reaction does not substantially increase as the ligand modified or ligand coated ferric hydroxide dissolves, and so results in comparatively low levels of sodium or potassium contamination in the final product as less sodium or potassium hydroxide is needed to dissolve the maltol slurry.

By way of illustration, at the start of the synthesis, the pH will preferably be above 8.0, more preferably above 8.5, and most preferably above 9.0. Generally, the pH will be below 12.0, more preferably below 11.6, and most preferably below 11.0. The pH can be adjusted with by addition of a base, preferably sodium hydroxide or sodium carbonate.

Generally, the ligand modified or ligand coated ferric hydroxide is added to a maltol solution at a concentration of 0.6M, 1.5M, 3M or greater. By way of illustration, the ligand modified or ligand coated ferric hydroxide is added to a maltol solution to achieve a maltol to iron ratio in solution equal to or greater than 3 and lower than 3.75, and more preferably a ratio between 3.1 and 3.5. Preferably, the ligand modified or ligand coated ferric hydroxide is added to a maltol solution which is at a pH above 8.0 and preferably greater than 8.5, and more preferably greater than 9.0.

It is also preferred that the ferric hydroxide is freshly precipitated, i.e. the ferric hydroxide is preferably used less than 96 hours, more preferably less than 48 hours, and most preferably less than 24 hours after its production. It is also preferred that the ferric hydroxide is not allowed to dry prior to being used in the synthesis of ferric trimaltol.

In a further aspect, the present invention provides a method of producing a ferric maltol composition which comprises the steps of:
  (a) mixing a ferric iron species with a ligand in solution;
  (b) precipitating a ligand modified ferric hydroxide slurry by raising the pH;
  (c) optionally removing and discarding a soluble fraction containing unwanted solutes, such as chloride, sodium or non-incorporated ligands;
  (d) optionally washing the retained pellet with water;
  (e) optionally re-suspending the pellet in water, or other appropriate solvents or solvent mixtures, and optionally adjusting pH;
  (f) reacting the ferric hydroxide with maltol to produce a ferric maltol composition;
  (e) recovering and optionally washing the ferric maltol composition; and
  (f) optionally drying and formulating the ferric maltol composition.

In a further aspect, the present invention provides a method of producing a ferric maltol composition which comprises the steps of:
  (a) preparing a ferric iron salt solution;
  (b) precipitating a ferric hydroxide colloid, or optionally a slurry, by raising pH;
  (c) mixing a ligand to produce a ligand-coated ferric hydroxide slurry
  (d) optionally removing and discarding a soluble fraction containing unwanted solutes, such as chloride, sodium or non-incorporated ligands;
  (e) optionally washing the retained pellet with water;
  (f) optionally re-suspending the pellet in water, or other appropriate solvents or solvent mixtures, and optionally adjusting pH;
  (g) reacting the ferric hydroxide with maltol to produce a ferric maltol composition;
  (h) recovering and optionally washing the ferric maltol; and
  (i) optionally drying the ferric maltol.

In a further aspect, the present invention provides a method for producing an iron supplement comprising ferric maltol, the process comprising having produced ferric maltol composition according to a method as described herein, the further step of formulating the ferric maltol for administration to a subject.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIGS. 1 and 2: UV vis conditions: Perkin Elmer Lambda 25; 700-350 nm; 480 nm/min; 0.5 nm interval.

DETAILED DESCRIPTION

Ferric Maltols

Figure 1:
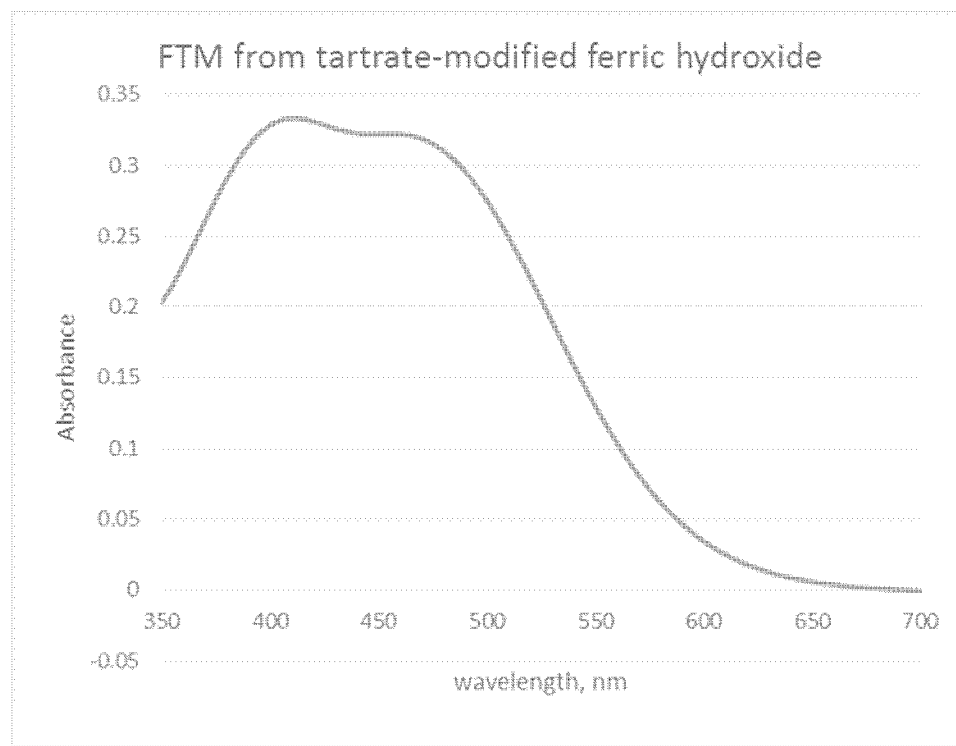
FIG. 1. UV-vis spectra of ferric trimaltol produced from tartrate-modified ferric hydroxide (as per Example 4). The two band profile is characteristic of ferric trimaltol recovered from an alkaline environment.
Figure 2:
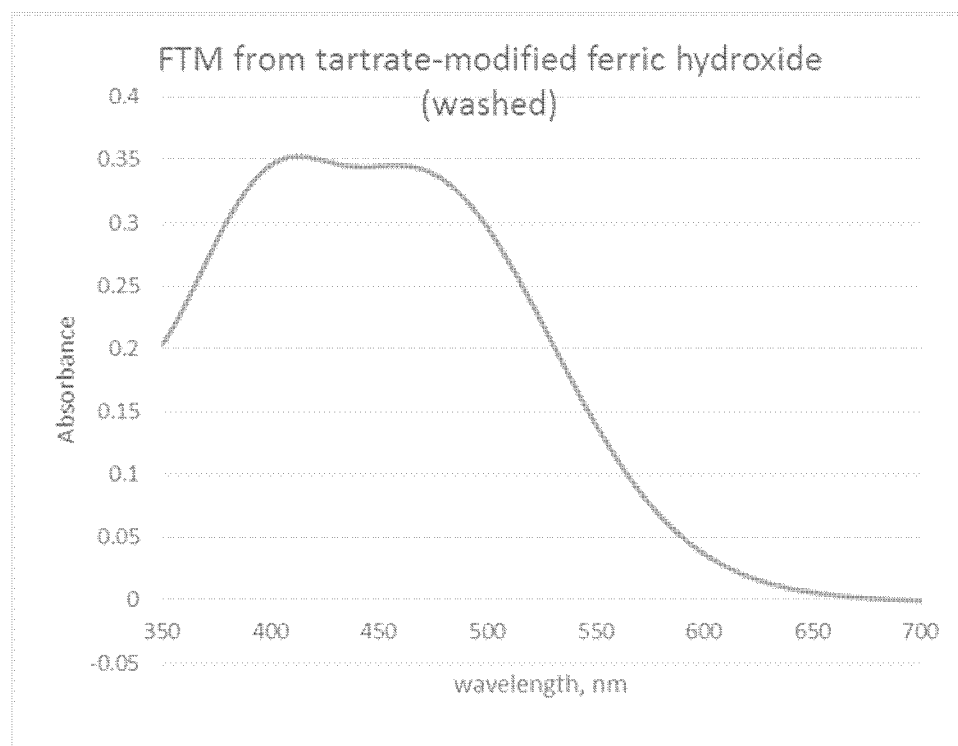
FIG. 2. UV-vis spectra of ferric trimaltol produced from tartrate-modified ferric hydroxide which had been previously washed (as per Example 5). The two band profile is characteristic of ferric trimaltol recovered from an alkaline environment.

Ferric maltols are a class of compounds that include ferric trimaltol, a chemical complex formed between ferric iron ($Fe^{3+}$) and the hydroxypyrone, maltol (IUPAC name: 3-Hydroxy-2-methyl-4H-pyran-4-one), in a molar ratio of ferric iron to maltol of 3:1. Maltol strongly chelates the ferric iron and the resulting complex (ferric trimaltol which may also be written as ferric tri-maltol) is well absorbed, in contrast to some other ferric iron supplements, fortificants and therapies. Maltol binds metal cations mainly in the form of a dioxobidentate ligand in a similar manner proposed for other 4(1H)-pyranones:

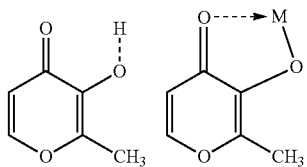

Structure of maltol (3-hydroxy-2-methyl-4(H)-pyran-4-one) and dioxo-chelation to metal cations (M) such as iron. For ferric trimaltol three maltol groups surround one iron.

However, particularly in aqueous environments, it is well known that concentration-dependent and pH-dependent equilibrium species of ferric maltol can form that include oligomeric species such as dimers and/or ferric iron species complexed with one or two maltol molecules. Ferric tri-maltol in solid or powder form may also exist as oligomers including dimers and not every iron is necessarily co-ordinated to three maltol molecules, but the term ferric tri-maltol is conventionally used in the art.

Accordingly, in the present application, references to "ferric maltol" are intended to include ferric iron species complexed with one, two or three maltol species, as well as oligomeric species such dimers and other species that may exist in equilibrium with them, and to mixtures of any of these species, even though the behaviour of the complex is believed to be dominated by its trimaltol form at supplemental levels.

The structure of ferric trimaltol is shown in WO 2015/101971 (Iron Therapeutics Holdings AG). Ferric trimaltol is also known as "ST10" and is generally administered as a 30 mg dose, where 30 mg refers to the amount of iron in the dose. The amount of ST10 equivalent to 30 mg of elemental iron ($Fe^{3+}$) is 231.5 mg. Ferric trimaltol has undergone clinical trials for the treatment or prevention of anaemia in particular in patients with inflammatory bowel disease (IBD) or in patients with intolerance of oral iron.

Ligand Modified and Ligand Coated Ferric Hydroxides

The production and characterisation of ligand modified metal oxo-hydroxides, such as ligand modified ferric hydroxides, is described in our earlier application WO 2008/096130, which is expressly incorporated by reference in its entirety. These approaches may also be employed to make the ligand modified ferric hydroxides used as one of the starting materials for making ferric trimaltol in the methods of the present invention. Ligand-coated materials are widely known in the art. These are distinct from ligand-modified materials, in that ligands are used to coat the particle surface rather than disrupt their mineral core. In the synthetic processes described herein, ferric hydroxides are coated with organic ligands, which increases the materials' dispersibility and/or reduces their drive towards aggregation.

WO 2008/096130 sets out that ligand modified metal oxo-hydroxides constitute forms of matter that differ from both conventional stoichiometric metal coordination complexes and from particles of metal hydroxide that have been physically coated with ligand molecules. Ligand modified metal hydroxides can be defined, inter alia, with reference to structural, spectroscopic or compositional parameters (i.e., using the analytical signatures of the materials) or by the processes by which the materials have been obtained. Thus, while metal hydroxide powders are very well known in the field of inorganic chemistry, when they are modified by suitable ligands (i.e. other than oxo or hydroxy groups) this may alter their physical and/or chemical properties to produce new materials and for use in new applications.

Ligand modified ferric hydroxides are formed when a ferric iron salt is dissolved and then induced to precipitate by an increase in pH leading to the formation of polymeric ferric hydroxide in the presence of one or more ligand species. This process results in some of the ligand species becoming incorporated into the solid phase structure of the ferric hydroxide.

By way of background, it is well known in the art that iron oxides, hydroxides and oxo-hydroxides are composed of Fe together with O and/or OH and are collectively referred to in this patent and known in the art as iron hydroxides. Different iron hydroxides possess different structures and elemental compositions which in turn determine their physicochemical properties (see Cornell & Schwertmann, The Iron Oxides Structure, Properties, Reactions, Occurrence and Uses. 2nd edition, 1996, VCH Publishers, New York). Without modification, the primary particles of the materials used herein are likely to have iron oxide cores and iron hydroxide surfaces and within different disciplines may be referred to as iron oxides or iron hydroxides or iron oxo-hydroxides or iron oxy-hydroxides or iron poly oxo-hydroxides or iron poly oxy-hydroxides. As described above, the materials of the present invention are altered at the level of the primary particle of the iron hydroxide with at least some of the ligand being introduced within the structure of the primary particle, i.e. leading to doping or contamination of the primary particle by the ligand. This may be contrasted with the formation of nano-mixtures of iron hydroxides and an organic molecule, such as iron saccharidic complexes, in which the structure of the primary particles is not so altered and the organic moiety is surface adsorbed. This may further be contrasted with the formation of conventional iron coordination complexes such as ferric citrate or ferric tartrate complexes which are stoichiometric.

The primary particles of the ligand modified ferric hydroxide used in the present invention may be produced by a process referred to as precipitation. The use of the term precipitation often refers to the formation of aggregates of materials that are capable of separation from solution by sedimentation or centrifugation. Here, the term "precipitation" is intended to describe the formation of all solid phase material, including aggregates as described above and solid materials that do not aggregate but remain as non-soluble moieties in suspension, whether or not they be particulate or nanoparticulate (colloidal or sub-colloidal).

In the present invention, the ligand modified ferric hydroxides are not generally crystalline and so have three dimensional polymeric or cross-linked structures that generally form above the critical precipitation pH used in their production. As used herein, this should not be taken as indicating that the structures of the materials are polymeric in the strict sense of having a regular repeating monomer unit because, as has been stated, ligand incorporation is, except by co-incidence, non-stoichiometric. The ligand species is introduced into the solid phase structure by substituting for oxo or hydroxy groups leading to a change in solid phase order. In the production of the ligand modified ferric hydroxides used in the methods of making ferric trimaltol, the ligand species may be introduced into the solid phase structure by the substitution of oxo or hydroxy groups by ligand molecules in a manner that decreases overall order in the solid phase material, so that the materials have a more amorphous nature compared, for example, to the structure of the corresponding unmodified ferric hydroxide. The presence of a more disordered or amorphous structure can readily be determined by the skilled person using techniques well known in the art. One exemplary technique is Transmission Electron Microscopy (TEM). High resolution transmission electron microscopy allows the crystalline pattern of the material to be visually assessed. It can indicate the primary particle size and structure (such as d-spacing), give some information on the distribution between amorphous and crystalline material. This may be especially apparent using high angle annular dark field aberration-corrected scanning transmission electron microscopy due to the high contrast achieved while maintaining the resolution, thus allowing the surface as well as the bulk of the primary particles of the material to be visualised.

Ligand Coated Ferric Hydroxide

Alternatively or additionally to using ligand modified ferric hydroxides as one of the starting materials for the synthesis of ferric trimaltol, the present invention may employ ligand coated ferric hydroxides. Ligand-coated ferric hydroxides comprise ferric hydroxide particles which were capped (i.e. surface coated through adsorption or similar means) with a ligand thus reducing their drive towards aggregation. In a further embodiment, ligand-coated materials may consist of aggregates (non-colloidal) which were capped to prevent or limit further aggregation. Unlike conventional metal coordination complexes, in ligand-coated materials the ligand is added at low, non-stoichiometric ratios and thus is not sufficiently concentrated to maintain or convert most of the iron to a soluble form.

The Ligand (L)

A range of ligands may be used in the production of the ligand modified or ligand coated ferric hydroxides used in the synthesis of ferric maltols, such as ferric trimaltol, in the methods of the present invention, and the ligand modified ferric hydroxides may comprise one, two, three, four or more different species of ligands. Typically, ligands are incorporated in the ligand modified ferric hydroxides to aid in the modification of a physico-chemical property of the material, e.g. as compared to unmodified or uncoated ferric hydroxides, in particular to aid in reaction that allows for the synthesis of ferric trimaltol. Examples of ligands that may be employed in the present invention include, but are by no means limited to: carboxylic acids such as adipic acid, glutaric acid, tartaric acid, malic acid, succinic acid, aspartic acid, pimelic acid, citric acid, gluconic acid, lactic acid or benzoic acid; food additives such as maltol, ethyl maltol or vanillin; amino acids such as lysine, tryptophan, glutamine, proline, valine, or histidine; and/or ionised forms thereof. Typically ligands may be well recognised in the art as having high affinity for a certain metal ion in solution or as having only low affinity or not be typically recognised as a ligand for a given metal ion at all. Typically, one ligand or two ligands of differing affinities for the metal ion are used in the production of these materials although zero, one, two, three, four, five or more different species of ligands may be useful in certain embodiments of the methods of the present invention.

The ligand may be a carboxylic acid ligand, or an ionised form thereof (i.e., a carboxylate ligand), such as tartaric acid or tartrate. A more preferred group of carboxylic acid ligands include tartaric acid or tartrate, adipic acid (or adipate), glutaric acid (or glutarate), pimelic acid (or pimelate), succinic acid (or succinate), and malic acid (or malate). A further preferred type of ligand are amino acids such as lysine, tryptophan, glutamine, proline, valine, or histidine.

Preferably, a low cost amino acid such as lysine is used in the synthesis. Whether the ligand is present as the acid or is partially or completely ionised and present in the form of an anion will depend on a range of factors such as the pH at which the material is produced and/or recovered, the use of post-production treatment or formulation steps and how the ligand becomes incorporated into the oxo-hydroxy metal ion material. In some embodiments with carboxylic acids, at least a proportion of the ligand will be present in the carboxylate form as the ferric hydroxide materials are typically recovered at pH >4 and because the interaction between the ligand and the positively charged iron would be greatly enhanced by the presence of the negatively charged carboxylate ion. For the avoidance of doubt, the use of carboxylic acid ligands in accordance with the present invention covers all of these possibilities, i.e. the ligand present as a carboxylic acid, in a non-ionised form, in a partially ionised form (e.g., if the ligand is a dicarboxylic acid) or completely ionised as a carboxylate ion, and mixtures thereof. Similarly, the use of the word amino acid covers all its possible ionisation forms. The molar ratio of the ferric ion(s) to the ligand(s) (L) is also a parameter of the solid phase ligand-modified poly oxo-hydroxy metal ion materials that can be varied according to the methods disclosed herein to vary the properties of the materials. Generally, the useful ratios of M:L will be between 10:1, 5:1, 4:1, 3:1, 2:1 and 1:1.

Ferric Maltol Compositions and their Uses

The ferric maltol compositions produced according to the methods of the present invention may be formulated for administration to an individual and contain in addition to ferric trimaltol, a pharmaceutically acceptable excipient, carrier, buffer, stabiliser or other materials well known to those skilled in the art. Such materials should be non-toxic and should not interfere with the efficacy of the solid phase materials for the application in question.

As described herein, ferric maltols, such as ferric trimaltol, have particular uses in the treatment of iron deficiency. By way of example, the ferric trimaltol compositions may be used to deliver iron to an individual for use in the prophylaxis or treatment of iron deficiency or iron deficiency anaemia which may be suspected, or diagnosed through standard haematological and clinical chemistry techniques. Iron deficiency and iron deficiency anaemia may occur in isolation, for example due to inadequate nutrition or due to excessive iron losses, or they may be associated with stresses such as pregnancy or lactation, or they may be associated with diseases such as inflammatory disorders, cancers and renal insufficiency. In addition, there is evidence that the reduced erythropoiesis associated with anaemia of chronic disease may be improved or corrected by the effective delivery of systemic iron and that co-delivery of iron with erythropoietin or its analogues may be especially effective in overcoming reduced erthropoietic activity. Thus, by way of further example, the ferric trimaltol compositions disclosed herein may be used to deliver iron to an individual for use in the treatment of sub-optimal erythropoietic activity such as in anaemia of chronic disease. Anaemia of chronic disease may be associated with conditions such as renal insufficiency, cancer and inflammatory disorders. As noted above, iron deficiency may also commonly occur in these disorders so it follows that treatment through iron supplementation may address iron deficiency alone and/or anaemia of chronic disease. It will be recognised by those skilled in the art that the above examples of the medical uses of iron supplements are by no means limiting.

In addition, ferric trimaltol is currently used for the treatment or prevention of anaemia in particular in patients with inflammatory bowel disease (IBD) or in patients with intolerance to other forms of oral iron.

The precise nature of the carrier or other component may be related to the manner or route of administration of the composition. These compositions may be delivered by a range of delivery routes including, but not limited to: gastrointestinal delivery, including orally and per rectum or by implantation at specific sites, including prosthetics that may be used for this purpose or mainly for another purpose but have this benefit.

Pharmaceutical compositions made according to the present invention are generally for oral administration and may be in a tablet, capsule, powder, gel or liquid form. A tablet may include a solid carrier such as gelatin or other excipients. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The ferric trimaltol compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual (e.g. bioavailability). The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

In general, ferric trimaltol may be used as a form of oral iron supplementation for nutritional or medical benefit. In this area, there are three main examples:

(i) Therapeutic (prescription) supplements, which are generally administered by the oral or i.v. routes for the treatment of indications including iron deficiency anaemia, iron deficiency and anaemia of chronic disease. The therapeutic administration of materials of the present invention may be in conjunction with other therapies and especially with the concomitant use of erythropoietin.

(ii) Nutritional (self prescribed/purchased supplements) which are usually for oral delivery.

(iii) Fortificants. These may be traditional forms—in terms of being added to food prior to purchase—or more recent fortificant forms such as 'Sprinkles' which are added (rather like salt or pepper) to food at the time of ingestion.

In all formats, but most especially for fortificants, subsequent formulation, such as addition of a protective coating (e.g. lipid), may be necessary to make the material compatible with its intended usage.

It will be recognised by those skilled in the art that the above examples of the medical uses of iron supplements are by no means limiting.

EXAMPLES

Example 1: Ferric Trimaltol from L-Lysine Coated Ferric Hydroxide

Synthesis of Lysine-Coated Ferric Hydroxide Colloid 14.87 g $FeCl_3.6H_2O$ was added to 25 mL UHP water and stirred until dissolved. 14.9 g NaOH 5M was then added drop-wise to this solution with constant stirring, during which a ferric hydroxide colloid was gradually produced. This colloidal suspension was then added to a L-Lysine suspension (5.02 g in 25 mL $ddH_2O$).

Ferric Trimaltol Synthesis 7 g NaOH pellets was added to 25 mL UHP water and stirred until dissolved. Next, 24.5 g maltol was added and stirred until dissolved. Then, the suspension of lysine-coated ferric hydroxide colloids was gradually added to the maltol with vigorous stirring, producing a dark red precipitate (with a significant brown hue). This suspension was incubated overnight during which time it became lighter and the brown hue disappeared. This precipitate was then recovered by centrifugation (4500 rpm×5 min) and dried overnight (50° C.).

Example 2: Ferric Trimaltol from L-Lysine Modified Ferric Hydroxide

Synthesis of Lysine-Modified Ferric Hydroxide Gel 14.87 g $FeCl_3.6H_2O$ and 5.02 g L-Lysine were added to 25 mL UHP water and stirred until dissolved. 32 mL NaOH 5M was then gradually added to this solution producing a ferric hydroxide gel.

Ferric Trimaltol Synthesis 7 g NaOH pellets was added to 25 mL UHP water and stirred until dissolved. Next, 24.5 g maltol was added and stirred until dissolved. Next, the lysine-modified ferric hydroxide gel was gradually added to this solution with vigorous stirring. A 1.2 M HCl solution was then used to drop the pH of the solution to 10, which was then incubated for 70 min. Finally, a dark red precipitate (i.e., ferric trimaltol) was recovered by centrifugation (4500 rpm×5 min) and dried overnight (45° C.).

Example 3: Absence of Ferric Hydroxide in Ferric Trimaltol

Ferric trimaltol is soluble in ethanol whereas ferric hydroxide (a potential contaminant) is not. As such ferric trimaltol powders produced as per Examples 1 and 2 were dissolved in ethanol. The material from Example 2 dissolved completely confirming the absence of iron hydroxides whereas the material from Example 1 did not. This supported the preference in the present invention for ligand modification, rather just surface coating, to ensure full conversion to ferric trimaltol.

Example 4: Ferric Trimaltol from Tartrate-Modified Ferric Hydroxide

Synthesis of Tartrate-Modified Ferric Hydroxide Gel 14.87 g $FeCl_3.6H_2O$ (0.055 mol) was added to 25 mL UHP water and stirred until dissolved. 4.12 g tartaric acid (0.0275 mol) was added to this solution and stirred until dissolved. 38 mL NaOH 5M was then gradually added to this solution producing a ferric hydroxide gel.

Ferric Trimaltol Synthesis 2 g NaOH pellets was added to 25 mL UHP water and stirred until dissolved. Next, 24.5 g maltol was added and stirred. This produced a slurry in which most of the maltol remained undissolved. Next, the tartrate-modified ferric hydroxide gel was gradually added to this solution with vigorous stirring during which the remainder of maltol dissolved. After 15 min a dark red precipitate (i.e. ferric trimaltol) had been formed and pH had stabilised at 8.5. The material was then washed by (1) centrifuging, (2) disposing of the supernatant and (3) resuspending in water back to its original volume. Finally, the material was recovered by centrifugation (4500 rpm×5 min) and dried overnight (50° C.).

Previously disclosed synthetic processes for the production of ferric trimaltol under aqueous conditions require the addition of NaOH (or other suitable bases) for conversion of maltol from its protonated form to its deprotonated form prior to complexation of iron. However this results in the formation of unwanted sodium ions which must be washed off. In contrast, the use of ferric hydroxides according to the methods of the present invention reduces the requirements for base and associated counter cation (e.g. sodium), which is a favourable feature. Note that ferric hydroxides are represented above as $Fe(OH)_3$ for illustrative purposes only. Different iron hydroxides possess different structures and elemental compositions (see Cornell & Schwertmann, The Iron Oxides Structure, Properties, Reactions, Occurrence and Uses. 2nd edition, 1996, VCH Publishers, New York).

Example 5: Ferric Trimaltol from Tartrate-Modified Ferric Hydroxide (with Removal of Contaminants from Ferric Hydroxide)

Material prepared as in Example 4, except excess reactants and reaction products (e.g. unbound tartaric acid, sodium chloride) were removed from the ferric hydroxide gel. This was achieved by centrifuging the ferric hydroxide gel after its synthesis and discarding the supernatant, which contained unwanted soluble species. Finally, the ferric hydroxide gel was re-suspended in water back to its original volume prior to being added to a maltol slurry.

Example 6: Ethanolic Clean Up for Ferric Trimaltol Produced from Ligand Coated Ferric Hydroxide Ferric trimaltol precipitate was purified as it contained an unwanted iron oxide fraction. Part of the wet pellet recovered by centrifugation (4.5 g) was dissolved in 1 L ethanol. The iron oxide fraction (which remained undissolved) was then removed by filtration, producing a turbidity-free solution. Next, ethanol was evaporated (40° C. in a rotavapor under vacuum) producing a concentrated ferric trimaltol slurry. This was then recovered and oven dried overnight at 50° C.

REFERENCES

All publications, patent and patent applications cited herein or filed with this application, including references filed as part of an Information Disclosure Statement are incorporated by reference in their entirety.

Gasche et al., Ferric maltol is effective in correcting iron deficiency anaemia in patients with inflammatory bowel disease: results from a phase-3 clinical trial program. *Inflamm Bowel Dis.*, 21(3):579-88, 2015.

Harvey et al., Ferric trimaltol corrects iron deficiency anaemia in patients intolerant of iron. *Aliment Pharmacol Ther.*, 12(9):845-8, 1998.

The invention claimed is:

1. A method for producing ferric trimaltol comprising reacting ligand-modified or ligand-coated ferric hydroxide with maltol and recovering the ferric trimaltol that forms, wherein the ligand is lysine or a tartaric acid or an ionized form thereof or a mixture thereof, and wherein the method comprises the steps of:
   (a) adding ferric chloride to water thereby to form a solution of ferric chloride;
   (b) gradually adding 5 molar sodium hydroxide to the solution of ferric chloride thereby to form a ferric hydroxide colloid;
   (c) adding the ferric hydroxide colloid to an aqueous solution or suspension of the ligand thereby to form a suspension of ligand-coated ferric hydroxide;
   (d) adding sodium hydroxide to water thereby to form a solution of sodium hydroxide;
   (e) adding maltol to the solution of sodium hydroxide thereby to form a solution of maltol; and (f) gradually adding the suspension of ligand-coated ferric hydroxide to the solution of maltol thereby to form a dark red precipitate of ferric trimaltol crystals, or wherein the method comprises the steps of:

(a') adding ferric chloride and the ligand to water thereby forming an aqueous solution of ferric chloride and ligand;

(b') gradually adding 5 molar sodium hydroxide to the aqueous solution of ferric chloride and ligand thereby to produce a ligand-modified ferric hydroxide gel;

(c') adding sodium hydroxide to water thereby to form a solution of sodium hydroxide;

(d') adding maltol to the solution of sodium hydroxide thereby to form a solution or slurry of maltol; and (e') gradually adding the ligand-modified ferric hydroxide to the solution of maltol, if necessary, adding hydrochloric acid to reduce the pH to 10, whereupon dark red crystals of ferric trimaltol precipitate, wherein the molar ratio of ferric iron to ligand is 10:1 to 1:1, wherein the maltol to ferric iron molar ratio is 3 to 3.75, wherein the ligand-coated ferric hydroxide is in the form of particles of ferric hydroxide coated on their surface with ligand, wherein the ligand-modified ferric hydroxide is in the form of particles of ferric hydroxide wherein the ligand is introduced into the solid phase structure of the particle by substituting for oxo or hydroxyl groups leading to a change in solid phase order.

2. The method according to claim 1, wherein the ferric hydroxide is ligand-modified ferric hydroxide.

3. The method according to claim 1, wherein the ferric hydroxide is ligand coated ferric hydroxide.

4. The method according to claim 1, wherein the reaction between the ligand-modified ferric hydroxide and maltol releases hydroxyl ions as the ferric iron ions are complexed by maltol, leading to further dissolution of maltol in the slurry of maltol.

5. The method according to claim 1, wherein the method is carried out under fully aqueous conditions.

6. The method according to claim 1, comprising producing the ligand-modified or ligand-coated ferric hydroxide from elemental iron, and optionally removing unreacted iron with a magnet.

7. The method according to claim 6, wherein the elemental iron is dissolved in a strong mineral acid.

8. The method according to claim 1, wherein ferric trimaltol is produced in a single vessel.

9. The method according to claim 1, further comprising separating, and optionally drying and/or formulating ferric trimaltol.

10. The method according to claim 1, further comprising mixing the ferric trimaltol with one or more excipients.

11. The method according to claim 1, further comprising formulating ferric trimaltol for administration to a subject.

12. The method according to claim 7, wherein the strong mineral acid is hydrochloric acid.

* * * * *